United States Patent
Angel et al.

(10) Patent No.: US 9,540,589 B2
(45) Date of Patent: Jan. 10, 2017

(54) FRAGRANCE COMPOSITION

(71) Applicant: Reckitt Benckiser (Brands) Limited, Slough, Berkshire (GB)

(72) Inventors: Nathan Angel, Basingstoke (GB); Simon Hurry, Ascot (GB)

(73) Assignee: Reckitt Benckiser (Brands) Limited, Slough, Berkshire (GB)

(*) Notice: Subject to any disclaimer, the term of this patent is extended or adjusted under 35 U.S.C. 154(b) by 63 days.

(21) Appl. No.: 14/294,583

(22) Filed: Jun. 3, 2014

(65) Prior Publication Data

US 2014/0364357 A1  Dec. 11, 2014

(30) Foreign Application Priority Data

Jun. 6, 2013 (GB) .................................. 1310108.4
May 30, 2014 (GB) .................................. 1409626.7

(51) Int. Cl.
  *C11B 9/00* (2006.01)
  *A61L 9/01* (2006.01)
(52) U.S. Cl.
  CPC ... *C11B 9/00* (2013.01); *A61L 9/01* (2013.01)

(58) Field of Classification Search
  CPC .......................................................... C11B 9/00
  See application file for complete search history.

(56) References Cited

U.S. PATENT DOCUMENTS 6,551,987 B1 * 4/2003 Miracle .................... A61K 8/41
                                                512/12

* cited by examiner

*Primary Examiner* — Ling Choi
*Assistant Examiner* — Lanee Reuther
(74) *Attorney, Agent, or Firm* — Troutman Sanders LLP; Ryan A. Schneider; Chris N. Davis

(57) ABSTRACT

A fragrance composition is described which comprises: at least two different fragrance accords wherein at least 30 wt % of each fragrance accord comprises the key contributor(s) of said fragrance accord and wherein the average of the odor detection thresholds of said key contributor(s) for each fragrance accord is within the same order of magnitude as the average of the odor detection thresholds of the key contributor(s) for said other fragrance accord(s); and wherein the base note(s) of each fragrance accord comprises less than 15% of the notes of said accord. Methods of manufacture thereof together with methods of attenuating fragrance habituation are also described.

57 Claims, 1 Drawing Sheet

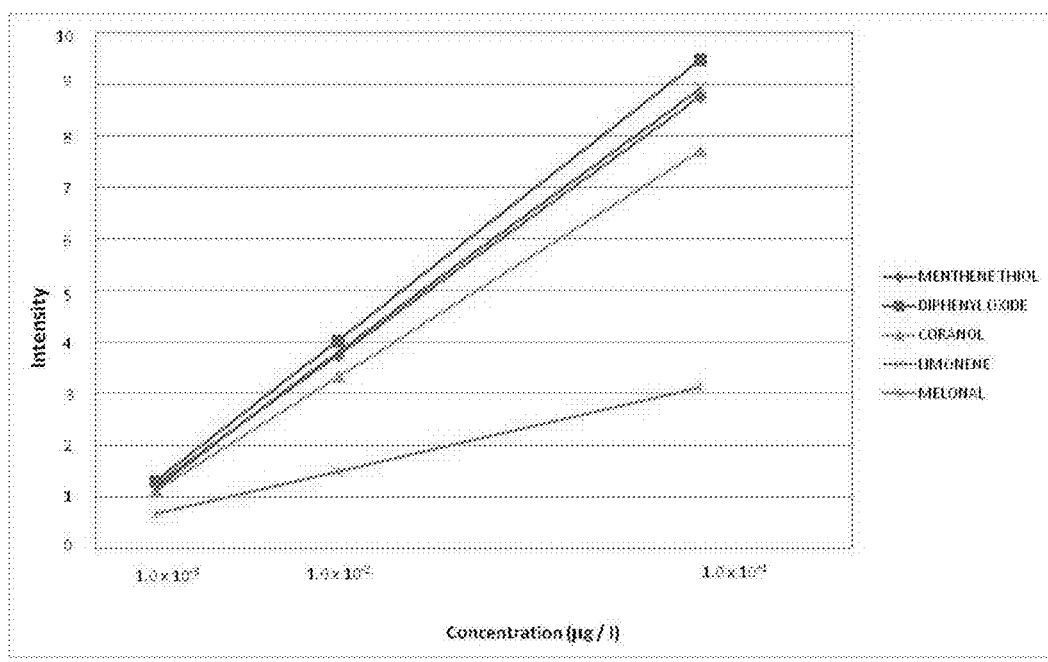

FRAGRANCE COMPOSITION

FIELD OF THE INVENTION

The present invention is related to the field of fragrance compositions and particularly, but not exclusively, fragrance compositions for use in fragranced consumer products including air freshening compositions.

BACKGROUND

All known fragrance composition comprise a single fragrance accord. A fragrance accord is a collection of raw materials that are used to create a specific olfactive odour that cannot be created from a single raw material and/or essential oil.

A fragrance accord is the olfactive theme or character of a fragrance and generally consists of a plurality of separate notes which in combination lose their individual identity to create a single odour or olfactive direction. The notes of a fragrance accord are defined by top notes, middle notes and base notes. Top notes represent the most volatile part of the accord these notes are usually perceived first by a human nose. The middle notes typically represent the "heart" of the accord as they often provide the majority of the fragrance. The base notes are typically the least volatile part of the accord and includes the heaviest molecules, therefore, the base note(s) usually linger for the longest period. A fragrance accord is typically made up of 10% top notes, 60% middle notes and 30% base notes.

When a perfumer wishes to make a fragrance accord that is indicative of a single core element, say rose, a perfumer would know that it would not be consumer-acceptable to simply provide diluted pure rose extract. In isolation pure rose extract has a "dry" and "slightly dirty" smell and certainly is not what a consumer would expect from a rose fragrance. Instead, a perfumer would blend several raw fragrance materials with the rose extract to make it more consumer-acceptable. Most likely the perfumer would select a raw material that imparts a "light green note" together with another raw material having a "slightly sweet note". Each of these different raw materials will have a different volatility (ie—will be one of a top note, middle note or bottom note). The perfumer would carefully blend these raw materials together to ensure that the combination of the rose extract, the light green note and slightly sweet note does not result in one note being clearly distinguishable from the others, rather the perfumer ensures that the raw materials are blended to work together simultaneously and harmoniously to produce a consumer-acceptable "rose" fragrance accord, i.e. a fragrance composition with a single fragrance accord, consisting of a rose fragrance accord. The resulting rose fragrance accord would then be blended with other non-fragrance accord components depending on the technical requirements of the overall fragrance composition.

Similarly, when a perfumer wishes to make a fragrance mixture that is indicative of two core elements, say rose and vanilla, the perfumer would not simply mix a fragrance accord for rose with a separate fragrance accord for vanilla on a 1:1 ratio since this would result in an unbalanced fragrance that would not be simultaneously indicative of the two accords, such a 1:1 ratio of fragrance accords would result in one fragrance accord completely dominating the other to render the less dominant fragrance accord completely or substantially completely imperceptible to a consumer. Instead, the perfumer attempting to make a fragrance composition indicative of these two core elements would carefully blend key raw materials indicative of the combination of rose and vanilla to create a single blended rose and vanilla fragrance accord. To do this a perfumer would have to confine themselves to a reduced palate of raw materials since any raw material indicative of rose and any raw material indicative of vanilla could only be used together to produce a rose and vanilla fragrance accord if they could be blended with each other in such a way that the raw materials would be complementary with each other olfactively to not result in one raw material being clearly distinguishable from the others. Instead the perfumer selects only certain raw material having notes which can be blended to work together to produce a single consumer-acceptable "rose & vanilla" fragrance accord, i.e. a fragrance composition with a single fragrance accord, consisting of a rose and vanilla fragrance accord.

Whereas a perfumer spends many years training in the art of creating perfumes and learning to distinguish olfactive features and understand the art of combining fragrance raw materials, a drawback of producing a balanced fragrance indicative of two core elements is that it can be difficult for a normal consumer that is not trained in olfactive matters to be able to distinguish the core elements either collectively or individually. For example, a normal consumer may think that the rose & vanilla fragrance discussed above has a "creamy & flowery" smell but would not necessarily be able to recognise that the perfumer has attempted to produce a fragrance that is simultaneously indicative of both rose and vanilla.

In addition to fragrance accords, a fragrance composition may also comprise other accords including MOC accords and/or functional/technical accords.

An MOC accord (malodour counteraction) is a collection of perfumery raw materials having a proven malodour counteraction capability that when added to a fragrance composition are intended to enhance the overall MOC performance.

A functional/technical accord is a collection of raw materials that form the main body of the fragrance when strict technical requirements are necessary, they can be both odiferous materials and solvents. One such technical requirement may relate to the mechanism by which the fragrance is to be emanated, this is often referred to as "trickle-down", by way of example in the case of continuous action emanation mechanisms strict control of viscosities and/or vapour pressures is required, or these accords may be present to assist in transportation through a hydrophobic membrane, or to solubilise in a polar base, or promote efficient and clean burning in a candle formulation.

An alternative mechanism to produce a consumer fragrance experience that is indicative of two core elements is to rely on a device to sequentially emanate separate fragrances at timed intervals from each other. Devices suitable for this include the AIRWICK® SYMPHONIA device which is configured to receive two separate bottles of fragrance and sequentially direct heat toward each bottle to accelerate the evaporation of fragrance therefrom. In such a device the fragrances contained in each bottle can be different to facilitate a consumer being able to notice the sequential nature of the fragrance emanation.

One advantage of devices such as the AIRWICK® SYMPHONIA device is that they can alleviate or ameliorate fragrance habituation; fragrance habituation can occur when a single fragrance remains in a vicinity at a substantially continuous concentration and a consumer becomes attenuated to it to such a degree that they can either no longer detect the fragrance or can only barely detect the fragrance.

In contrast a drawback is that such anti-habituation devices are limited in applicability since they are only suitable for particular automated emanation mechanisms, such as using heat directed at a wick in fluid contact with liquid fragrance, and less suited for use with auto-spray mechanisms due to the size of device needed to accommodate two separate containers of fragrance such as two separate aerosols of fragrance. Such anti-habituation devices are not applicable to non-automated emanation devices including passive fragrance emanators (ie—a fragrance emanator possessing no powered means to facilitate emanation, such as a reed diffuser or a fragrance gel emanator) or a fragranced candle or the like. The present invention seeks to provide a consumer fragrance experience that is indicative of at least two equally distinguishable fragrance accords without having to formulate them into a single blended fragrance accord only indicative for the core elements or without relying on a device to sequentially emanate separate fragrances.

SUMMARY OF INVENTION

According to a first aspect of the present invention there is provided therefore a fragrance composition comprising:

at least two different fragrance accords wherein at least 30 wt % of each fragrance accord comprises the key contributor(s) of said fragrance accord and wherein the average of the odour detection thresholds of said key contributor(s) for each fragrance accord is within the same order of magnitude as the average of the odour detection thresholds of the key contributor(s) for said other fragrance accord(s).

Odour detection threshold, hereinafter referred to as ODT, gives a quantitative representation of minimum levels at which a human population detects a fragrance raw material. ODT is determined by several factors including the molecule's shape, polarity, partial charges, stereochemistry and molecular mass. The olfactory mechanisms in a human nose responsible for a raw material's detection threshold is not well understood and cannot be accurately predicted, therefore, testing to determine the ODT of a raw material is measured through extensive human sensory testing wherein trained testers are exposed to decreasing amounts of the odour until only 50% of the population of testers are able to detect the presence of the odour. Although the ODT of most raw materials is a low concentration, interestingly a concentration of only 10 to 50 times above the ODT concentration is typically the maximum intensity that can be detected by humans, whereas the maximum intensity of sight in humans is typically about 500,000 times that of the corresponding optical intensity. As such, smell is often concerned with identifying the presence or absence of a particular odour rather than quantifying the intensity or concentration thereof.

"Key contributor" of a fragrance accord is characterised herein as the raw material(s) in a fragrance accord that are most synonymous with the essential elements of the olfactive identity of the accord. The skilled person, namely a trained perfumer, will understand that a fragrance accord is composed from a collection of raw materials that will typically number between 6-20 different materials but that typically only a minority of those materials will be a key contributor.

Most trained perfumers will know whether a particular raw material is a key contributor for a particular fragrance accord or not. However, since perfume creation is part-science and part-artistry and since there is no prescribed definition for when a specific raw material is a key contributor for a specific fragrance accord or not, inherently there will always be a small margin for subjectivity regarding whether every trained perfumer would always consider a specific raw ingredient to represent a key contributor for a specific fragrance accord or not. Nevertheless, for the skilled person, such as a trained perfumer, reading the contents of this specification as a whole together with their common general knowledge following their training as perfumer and armed with a mind to understand it would not present undue burden to experiment with any raw material around which there was such subjectivity.

The inventors of the present invention have, surprisingly, found that despite contravening standard perfumery convention of creating a balanced fragrance composition possessing a single balanced olfactive direction, it is possible to make an unbalanced fragrance composition in a measured way in accordance with the present invention that exhibits the odour of each fragrance accord substantially simultaneously and/or substantially sequentially throughout the life or the majority of the life of the fragrance composition sufficiently clearly to be distinguishable by an average consumer rather than just to a trained perfumer. In other words to the average consumer the fragrance composition of the present invention will be indicative of a single fragrance accord at any point in which they are smelling the fragrance, but the particular fragrance accord they can detect will vary over time depending of the dissipation of each fragrance accord relative to each other as defined by their respective odour slopes, discussed in detail later. Therefore, fragrance compositions in accordance with the present invention are able to provide a consumer fragrance experience that is indicative of at least two distinguishable fragrances without blending them into a fragrance composition possessing a single olfactive direction and without relying on a device to sequentially emanate separate fragrance compositions.

Preferably the fragrance composition is provided with at least three fragrance accords. Even more preferably the fragrance composition is provided with between two to five fragrance accords. Most preferably however, the fragrance composition is provided with three fragrance accords. Whilst the fragrance composition can in theory be provided with any number of differing fragrance accords, the higher the number of accords the more difficult it will be to find accords that will blend satisfactorily with each other and the more difficult it will be for an average consumer to distinguish between the accords. Three different fragrance accords are considered to be the optimum number of accords since that permits a sufficiently board range of olfactive directions to be selected for mixing as well as allowing an average consumer to easily distinguish between said accords.

Preferably the base note(s) of the fragrance accords comprise less than 15% of the notes of said accord. Even more preferably the base note(s) of the fragrance accords comprise less than 12.5% of the notes of said accord, and even more preferably the base note(s) of the fragrance accords comprise less than 10% of the notes of said accord, and most preferably the base note(s) of the fragrance accords comprise substantially 7.5%+/−1.5% of the notes of said accord.

Most trained perfumers will know whether a particular raw material is classified as a base note or not. However, since there is no prescribed definition for the boundaries between base notes/middle notes/top notes inherently there will always be a small margin for subjectivity regarding whether every trained perfumer would always consider a specific raw ingredient to represent a top, middle or base note or not. Nevertheless, for the skilled person, such as a trained perfumer, reading the contents of this specification as a whole together with their common general knowledge following their training as perfumer and armed with a mind to understand it would not present undue burden to experiment with any raw material around which there was such subjectivity.

Since the base note(s) of the fragrance accords preferably comprise less than 15% of the notes of said accord, the middle notes and top notes preferably jointly comprise at least 85% of the notes of said accord. It is particularly preferred for the middle note(s) of the fragrance accords to comprise greater than 30% of the notes of said accord and the top note(s) of the fragrance accords comprise greater than 30% of the notes of said accord, wherein the % of notes of the overall accord equals 100%. More preferably the middle note(s) of the fragrance accords comprise greater than 35% of the notes of said accord and the top note(s) of the fragrance accords comprise greater than 35% of the notes of said accord, wherein the % of notes of the overall accord equals 100%. Most preferably the middle note(s) of the fragrance accords comprise greater than 40% of the notes of said accord and the top note(s) of the fragrance accords comprise greater than 40% of the notes of said accord, wherein the % of notes of the overall accord equals 100%.

Each fragrance raw material within an accord has an odour slope which describes how the intensity of the of the odour decreases as the concentration diminishes over time. Typically odour slopes are expressed graphically with intensity on the y-axis (1-10) and concentration on the x-axis (μg/L) and their gradient defines the odour slope. Preferably the odour slope of each fragrance accord in the fragrance composition has a similar gradient. FIG. 1 shows the odour slopes of five fragrance raw materials, namely: menthene thiol; diphenyl oxide, limonene, coranol and melonal and it can be seen that apart from melanol they all exhibit different but similar odour slopes, whereas melanol exhibits a non-similar odour slope. Within the context of the present invention a "similar" gradient is understood to preferably mean gradients within 50% of each other. Referring to FIG. 1, the gradient of the odour slope of diphenyl oxide is 82.83, the gradient of the odour slope of coranol is 66.67, these gradients are within 50% of each other and thus are considered to be similar. Whereas the gradient of the odour slope of melonal is 24.24 which is not within 50% of either of the gradients of the odour slopes of diphenyl oxide or coranol, thus the odour slope is non-similar. Within the context of the present invention a "similar" gradient is, more preferably, understood to mean gradients within 40% of each other, and even more preferably understood to mean within 30% of each other.

Different emanation formats may present different formulation challenges. For instance a fragrance that is an 'instant action' format, such as an automatic aerosol format where the aerosol formulation contents are equally dispersed and held under pressure, this format will permit each fragrance accord to be released equally regardless of the volatility thereof. In contrast, for 'continuous action' formats, such as using a wick delivery system to deliver the liquid via wicking action to a heater for volatilisation, the volatility is much more critical.

Where the emanation format is volatility-sensitive preferably the volatility of the top, middle and base notes of each fragrance accord is similar. More preferably the volatility of the top, middle and base notes of each fragrance accord is defined according to the following formula, namely:
Top notes=>40% with a vapour pressure>0.1 mmHg;
Middle notes=>40% with a vapour pressure range of between 0.1 mmHg-0.001 mmHg; and
Base notes=>5% with a vapour pressure<0.001 mmHg.

Even more preferably the volatility of the top, middle and base notes of each fragrance accord is defined according to the following formula, namely:
Top notes=>45% with a vapour pressure>0.1 mmHg;
Middle notes=>42.5% with a vapour pressure range of between 0.1 mmHg-0.001 mmHg; and
Base notes=>6% with a vapour pressure<0.001 mmHg.

Most preferably the volatility of the top, middle and base notes of each fragrance accord is defined according to the following formula, namely:
Top notes=~47.5% with a vapour pressure>0.1 mmHg;
Middle notes=~45% with a vapour pressure range of between 0.1 mmHg-0.001 mmHg; and
Base notes=~7.5% with a vapour pressure<0.001 mmHg.

It is an essential requirement that at least 30 wt % of each fragrance accord comprises the key contributor(s) of said fragrance accord and that the average of the ODT thresholds of said key contributor(s) must be within the same order of magnitude as the average of the ODT thresholds key contributor(s) for the other fragrance accords. Preferably in the remaining % of the fragrance accord prominent olfactive notes that have a tendency to overpower the at least the key contributor(s) of the accord are avoided. The skilled person in the art of perfumery will be aware of such prominent olfactive notes and will understand the location of same, such that if the location of said prominent olfactive note is not within the the key contributor(s) of the fragrance accord the accord will most likely be incompatible with the compositions of the present invention and/or that fragrance accord may require reformulation to minimise or remove the prominent olfactive note.

The key contributor(s) of each fragrance accord have an odour contribution and preferably the odour contribution of the key contributors is similar. Odour contribution is expressed as ODT/vapour pressure and is a measure of the noticability of a raw material. Understanding the odour contribution of the raw materials used in the fragrance compositions of the present invention can be used to fine tune the creation of the composition by allowing a perfumer to determine that a particular raw material may have a particularly high or low odour contribution and the perfumer can determine how best to include same. For instance, if a raw material having a high level of odour contribution was to be considered for use in a composition according to the present invention and it was not a key contributor in one of the fragrance accords, then the perfumer may elect not to include it as the high level of its odour contribution may cause it to olfactively interfere with the fragrance accords, or the perfumer may only include it in a relatively small amount.

Other components that may be present in the fragrance compositions of the present invention include one or more of: solvents; free radical scavengers; U.V inhibitors; dyes; etc.

The fragrance compositions of the present invention may comprise >99% wt of fragrance accords. Preferably each fragrance accord in the fragrance composition of the present invention may comprise of between 5-49.9% wt of the composition. More preferably each fragrance accord in the fragrance composition of the present invention may comprise of between 5-33% wt of the composition. Even more preferably each fragrance accord in the fragrance composition of the present invention may comprise of between 5-30% wt of the composition.

The fragrance compositions of the present invention may comprise between 0-90% wt of technical accords. Preferably the fragrance compositions of the present invention may comprise between 1-90% wt of technical accords. More preferably the fragrance compositions of the present invention may comprise between 10-95% wt of technical accords. Even more preferably the fragrance compositions of the present invention may comprise between 20-85% wt of technical accords.

Non-limiting examples of technical accord raw materials include: Benzyl Acetate; Benzyl Alcohol (Phenyl Methanol); Linalol (3,7-Dimethyl-1,6-Octadien-3-Ol); Linalyl Acetate (1,5-Dimethyl-1-Vinyl-4-Hexenyl Acetate); Dipropylene Glycol Monomethyl Ether (1-(2-Methoxypropoxy)-2-Propanol); Tripropylene Glycol monomethyl ether ((2-(2-Methoxymethylethoxy)methylethoxy)propanol; Isopar™ M (Isoparaffinic Hydrocarbon distillate); Isopropyl Myristate (3,7-Dimethyl-1,6-Octadien-3-Ol); Benzyl Benzoate; Isobornyl Acetate (1,7,7-Trimethyl-Bicyclo[2.2.1]Hept-2-yl Acetate).

The fragrance compositions of the present invention may comprise between 0-20% wt of MOC accords. Preferably the fragrance compositions of the present invention may comprise between 0-15% wt of MOC accords. More preferably the fragrance compositions of the present invention may comprise between 0-10% wt of MOC accords. Non-limiting examples of MOC accord raw materials include raw materials that are known to reduce the perception of malodours such as various combinations of aldehydes and/or other known MOC accord raw materials.

The fragrance compositions of the present invention may comprise between 0-10% wt of UV inhibitor(s). Preferably the fragrance compositions of the present invention may comprise between 0-4% wt of UV inhibitor(s).

The fragrance compositions of the present invention may comprise between 0-5% wt of antioxidant(s). Preferably the fragrance compositions of the present invention may comprise between 0-2% wt of antioxidant(s).

The fragrance compositions of the present invention may comprise between 0-1% wt of dye(s). Preferably the fragrance compositions of the present invention may comprise between 0-0.5% wt of dye(s).

Preferably a backbone is provided in the composition, wherein said backbone may comprise odiferous materials, bulk carriers and/or solvents which can be varied depending on the olfactive combination of the fragrance accords and technical requirements of the fragrance composition. The purpose of the backbone is to provide a foundation to the fragrance accords to facilitate the final fragrance composition to be detected as olfactively complete and well-rounded. Here "complete and well-rounded" is understood to mean that if the creator of a fragrance composition wishes to create a composition possessing two or more fragrance accords wherein rather than having the two accords stand out against each other olfactively a background or baseline of fragrance may be provided to olfactively smooth the transition between the fragrance accords, thus impacting the overall experience of the fragrance. Backbone materials may be materials that are also classified as a fragrance accord raw material or as a technical accord raw material. However a backbone material that could also be classified as a fragrance accord raw material would not be a key contributor for a fragrance accord. Due to this purpose therefore, it is essential that any components of the backbone complement the overall perception or the performance of the fragrance accords. The backbone components may have varying ODTs relative to each other and to the fragrance accords, however, since any backbone component must possess an odour contribution which does not substantially interrupt nor substantially interfere with the balance between the fragrance accords, the resultant consumer fragrance experience that is dynamically indicative of each respective fragrance accord over time is not disrupted.

Non-limiting examples of materials that may be useful as a backbone material include: Benzyl Acetate; Ethyl Acetoacetate (Ethyl 3-Oxobutanoate); Linalyl Acetate (1,5-Dimethyl-1-Vinyl-4-Hexenyl Acetate); Dartanol ((−)-(1'r,E)-2-Ethyl-4-(2',2',3'-Trimethyl-3'-Cyclopenten-1'-yl)-2-Buten-1-Ol); Verdox (2-T-Butyl Cyclohexyl Acetate); Citral (3,7-Dimethyl-2,6-Octadienal); Coumarin (2-Chromenone); Zestover (2,4-Dimethyl-3-Cyclohexene-1-Carboxaldehyde); Dihydromyrcenol ((+−)-2,6-Dimethyl-7-Octen-2-Ol); Iso E super (1,2,3,4,5,6,7,8-Octahydro-1,1,6,7-Tetramethyl-7-Acetyl Naphthalene); Limonene (1-Methyl-4-(1-methylethenyl)-cyclohexene); Hexyl Acetate; Benzyl Benzoate; Neononyl Acetate (3,5,5-Trimethylhexyl Acetate); Pipol (distilled); Dowanol TPM; Isopar M; Linalol.

According to a second aspect of the present invention there is provided therefore a method of making a fragrance composition having at least two different fragrance accords comprising the steps of:

matching said at least two fragrance accords by providing that at least 30% wt of the key contributor(s) of each fragrance accord has an average odour detection threshold within the same order of magnitude as each other fragrance accord.

According to a third aspect of the present invention there is provided therefore a method of attenuating fragrance habituation comprising the steps of emanating a fragrance composition comprising at least two different fragrance accords and wherein said fragrance composition comprises:

at least two different fragrance accords wherein at least 30 wt % of each fragrance accord comprises the key contributor(s) for said fragrance accord and wherein the average of the odour detection thresholds of said key contributor(s) for each fragrance accord is within the same order of magnitude as the average of the odour detection thresholds of the key contributor(s) for said other fragrance accord(s).

According to a fourth aspect of the present invention there is provided therefore a multi-fragrance accord fragrance composition comprising:

three different fragrance accords wherein at least 30 wt % of each fragrance accord comprises the key contributor(s) of said fragrance accord and wherein the average of the odour detection thresholds of said key contributor(s) for each fragrance accord is within the same order of magnitude as the average of the odour detection thresholds of the key contributor(s) for said other fragrance accord(s).

Any of the features described herein may be combined with any of the above aspects in any combination.

DESCRIPTION OF AN EMBODIMENT

Embodiments of the fragrance compositions according to the present invention will now be described, by way of example only. Each of the following examples relate to fragrance compositions comprising at least two fragrance accords which have been formulated to be suitable for use with an electrical diffuser. An electrical diffuser comprises a heater adjacent a chimney or the like and fragrance containers suitable for use with such diffusers possess a liquid reservoir with a wick inserted therein which extends out of the reservoir to protrude above the container such that, in use, the end of the wick distal to the reservoir extends into the chimney to be adjacent the heater to allow the heat emitted therefrom to evaporate the liquid from the wick into the surrounding environment.

EXAMPLE 1

A fragrance composition was produced from the combination of three separate fragrance accords wherein the fragrance accords where indicative of marshmallow, raspberry and rose respectively.

| Fragrance Raw Material | Accord | % wt | ODT (µg/L) | Note Type |
|---|---|---|---|---|
| Phenyl ethyl alcohol* | Rose | 3.56 | $3.02 \times 10^{-4}$ | Middle |
| Clove oil* | Rose | 0.22 | $6.21 \times 10^{-4}$ | Middle |
| Rose Oxide* | Rose | 0.12 | $9.77 \times 10^{-4}$ | Middle |
| Doremox* | Rose | 0.12 | $3.04 \times 10^{-4}$ | Middle |
| 5 additional raw materials all non-key contributors | Rose | 5.77 (Range 4.51-0.04) | (Range $3.05 \times 10^{-2}$-$3.70 \times 10^{-5}$) | Mixture of top, middle & base |
| Vanillin* | Marshmallow | 1.41 | $3.06 \times 10^{-5}$ | Base |
| Ethyl Praline* | Marshmallow | 0.51 | $4.45 \times 10^{-5}$ | Middle |
| Ethyl vaniline* | Marshmallow | 0.44 | $4.10 \times 10^{-5}$ | Middle |
| Nussol Extra* | Marshmallow | 0.12 | $5.26 \times 10^{-4}$ | Middle |
| 7 additional raw materials all non-key contributors | Marshmallow | 5.41 (Range 1.73-0.25) | (Range $3.13 \times 10^{-3}$-$4.81 \times 10^{-5}$) | Mixture of top, middle & base |
| Raspberry ketone* | Raspberry | 1.97 | $5.05 \times 10^{-7}$ | Middle |
| Beta Ionone* | Raspberry | 0.05 | $4.07 \times 10^{-4}$ | Middle |
| Dodecalactone* | Raspberry | 0.12 | $3.37 \times 10^{-4}$ | Middle |
| 6 additional raw materials all non-key contributors | Raspberry | 4.99 (Range 1.84-0.04) | (Range $0.0332$-$1.16 \times 10^{-5}$) | Mixture of top, middle & base |
| Ethyl Acetoacetate | Technical | 24.47 | $2.80 \times 10^{-2}$ | n/a |
| Dowanol TPM | Technical | 21.37 | N/A | n/a |
| Dowanol DPNP | Technical | 14.23 | N/A | n/a |
| Benzyl Acetate | Technical | 7.49 | $7.24 \times 10^{-3}$ | n/a |
| Linalol | Technical | 7.63 | $6.89 \times 10^{-5}$ | n/a |
| TOTAL | | 100.00 | | |

(*= a key contributor)

Matched ODT Values

Rose accord=41% of the accord is made up of the key contributors therefor and they have an average ODT of $5.51 \times 10^{-4}$ µg/l Marshmallow accord=31% of the accord is made up of the key contributors therefor and they have an average ODT of $1.60 \times 10^{-4}$ µg/l Raspberry accord=30% of the accord is made up of the key contributors therefor and they have an average ODT of $2.48 \times 10^{-4}$ µg/l To determine the average of the ODTs for the key contributors of each fragrance accord the ODT of each key contributor within a single fragrance accord was added together and divided by the number of key contributors within that fragrance accord.

Ratio of Notes and their Vapour Pressure

In Example 1 the top, middle and base notes were as follows:

Top—47.5% of the notes with a vapour pressure of >0.1 mmHg

Middle—45% of the notes with a vapour pressure of 0.1 mmHg-$1.0 \times 10^{-3}$ mmHg Base—7.5% of the notes with a vapour pressure of $<1.0 \times 10^{-3}$ mmHg The three fragrance accords all have similar odour slopes and were substantially devoid of any prominent olfactive notes in the non-key contributors of each fragrance accord.

The three fragrance accords were compatible within the context of the present invention as at least 30% of each fragrance accord comprised the key contributors within that fragrance accord and the average ODT thresholds of the key contributors within each accord are of the same order of magnitude as average ODT thresholds of the key contributors of the other fragrance accords. Also each fragrance accord had base notes that made up less than 15% of the notes of that accord and resulted in the fragrance composition, as a whole, comprising bases notes that were less than 15% of the notes of said composition.

Backbone components comprised odiferous materials having ave. ODT values ranging from $1.40 \times 10^{-2}$ µg/l to $2.71 \times 10^{-5}$ µg/l, bulk carriers having ave. ODT values ranging from $4.10 \times 10^{-3}$ µg/l to $2.00 \times 10^{-5}$ µg/l and solvents not having ODT values wherein none of the backbone components possessed an odour contribution which does not interfere with the overall perception or performance of the fragrance accords.

The fragrance was allowed to emanate within a sensory booth before a panel of experienced sensory panels were exposed as part of a blind, balanced, randomised and sequential monadic testing protocol thereto. The panel comprised a minimum of 20 panelists, both male and female. Example 1 was presented alongside conceptually matched distinctive olfactive concepts designating rose, marshmallow and berry and every time a panellist was exposed to the booth they were asked to record which olfactive concept they smelt. When they declared that they smelt a different olfactive concept to the olfactive concept they had declared previously this was (unbeknown to the panellist) recorded as a "switch".

There was a theoretical distribution of 100% switches and 0% non-switches at the conclusion of the testing but the expected/practical distribution to be indicative of a fragrance presenting more than one distinctive fragrance accord was 70% switches and 30% non-switches. The recorded results were subjected to a chi-squared test.

The obtained results showed that Example 1 is significantly validated as a multi-fragrance accord fragrance @95% confidence level.

EXAMPLE 2

A fragrance composition was produced from the combination of three separate fragrance accords wherein the accords where indicative of red berry, gourmand and watermint respectively.

Matched ODT Values

Red Berry accord=73% of the accord is made up of the key contributors therefor and they have an average ODT of $1.23 \times 10^{-4}$ µg/l Gourmand accord=32% of the accord is made up of the key contributors therefor and they have an average ODT of $1.54 \times 10^{-4}$ µg/l Watermint accord=35% of the accord is made up of the key contributors therefor and they have an average ODT of $2.24 \times 10^{-4}$ µg/l To determine the average of the ODTs for the key contributors of each fragrance accord the ODT of each key contributor within a single fragrance accord was added together and divided by the number of key contributors within that fragrance accord.

The three fragrance accords were compatible within the context of the present invention as at least 30% of each fragrance accord comprised the key contributors within that fragrance accord and the average ODT thresholds of the key contributors within each accord are of the same order of magnitude as average ODT thresholds of the key contributors of the other fragrance accords. Also each fragrance accord had base notes that made up less than 15% of the notes of that accord and resulted in the fragrance composition, as a whole, comprising bases notes that were less than 15% of the notes of said composition.

As with Example 1, the fragrance of Example 2 was allowed to emanate within a sensory booth before a panel of experienced sensory panels were exposed as part of a blind, balanced, randomised and sequential monadic testing protocol thereto. The panel comprised a minimum of 20 panelists, both male and female. Example 2 was presented alongside conceptually matched distinctive olfactive concepts designating berry, gourmand and watermint and every time a panellist was exposed to the booth they were asked to record which olfactive concept they smelt. When they declared that they smelt a different olfactive concept to the olfactive concept they had declared previously this was (unbeknown to the panellist) recorded as a "switch".

There was a theoretical distribution of 100% switches and 0% non-switches at the conclusion of the testing but the expected/practical distribution to be indicative of a fragrance presenting more than one distinctive fragrance accord was 70% switches and 30% non-switches. The recorded results were subjected to a chi-squared test.

The obtained results showed that Example 2 is significantly validated as a multi-fragrance accord fragrance @95% confidence level.

EXAMPLE 3

Example 3 is a modified version of Example 1 wherein some of the key contributors of the fragrance accords were modified either by substitution, addition or a change in quantity thereof with the aim to render the fragrance accords as collectively more prominent olfactively against the backbone, the backbone components were unchanged.

| Fragrance Raw Material | Accord | % wt | ODT (µg/L) | Note Type |
|---|---|---|---|---|
| Phenyl ethyl alcohol* | Rose | 2.34 | $3.02 \times 10^{-4}$ | Middle |
| Clove oil* | Rose | 0.22 | $6.21 \times 10^{-4}$ | Middle |
| Rose Oxide* | Rose | 0.10 | $9.77 \times 10^{-4}$ | Middle |
| Geraniol* | Rose | 0.24 | $5.40 \times 10^{-4}$ | Middle |
| 5 additional raw materials all non-key contributors | Rose | 5.87 (Range 4.51-0.04) | (Range $3.05 \times 10^{-2}$-$3.70 \times 10^{-5}$) | Mixture of top, middle & base |
| Vanillin* | Marshmallow | 2.17 | $3.06 \times 10^{-6}$ | Base |
| Ethyl Praline* | Marshmallow | 0.51 | $4.45 \times 10^{-5}$ | Middle |
| Ethyl vaniline* | Marshmallow | 0.78 | $4.10 \times 10^{-5}$ | Middle |
| Nussol Extra* | Marshmallow | 0.12 | $5.26 \times 10^{-4}$ | Middle |
| 7 additional raw materials all non-key contributors | Marshmallow | 5.41 (Range 1.73-0.25) | (Range $3.13 \times 10^{-3}$-$4.81 \times 10^{-5}$) | Mixture of top, middle & base |
| Raspberry ketone* | Raspberry | 1.24 | $5.05 \times 10^{-7}$ | Middle |
| Beta Ionone* | Raspberry | 0.52 | $4.07 \times 10^{-4}$ | Middle |
| Dodecalactone* | Raspberry | 0.12 | $3.37 \times 10^{-4}$ | Middle |
| Ethyl Caproate* | Raspberry | 0.27 | $5.25 \times 10^{-4}$ | Top |
| 6 additional raw materials all non-key contributors | Raspberry | 4.99 (Range 1.84-0.04) | (Range 0.0332-$1.16 \times 10^{-5}$) | Mixture of top, middle & base |
| Ethyl Acetoacetate | Technical | 24.47 | $2.80 \times 10^{-2}$ | n/a |
| Dowanol TPM | Technical | 21.28 | N/A | n/a |
| Dowanol DPNP | Technical | 14.23 | N/A | n/a |
| Benzyl Acetate | Technical | 7.49 | $7.24 \times 10^{-3}$ | n/a |
| Linalol | Technical | 7.63 | $6.89 \times 10^{-5}$ | n/a |
| TOTAL | | 100.00 | | |

(*= a key contributor)

Matched ODT Values

Rose accord=33% of the accord is made up of the key contributors therefor and they have an average ODT of $6.10 \times 10^{-4}$ µg/l Marshmallow accord=40% of the accord is made up of the key contributors therefor and they have an average ODT of $1.60 \times 10^{-4}$ µg/l Raspberry accord=30% of the accord is made up of the key contributors therefor and they have an average ODT of $3.17 \times 10^{-4}$ µg/l To determine the average of the ODTs for the key contributors of each fragrance accord the ODT of each key contributor within a single fragrance accord was added together and divided by the number of key contributors within that fragrance accord.

The three fragrance accords were compatible within the context of the present invention as at least 30% of each fragrance accord comprised the key contributors within that fragrance accord and the average ODT thresholds of the key contributors within each accord are of the same order of magnitude as average ODT thresholds of the key contributors of the other fragrance accords. Also each fragrance accord had base notes that made up less than 15% of the notes of that accord and resulted in the fragrance composition, as a whole, comprising bases notes that were less than 15% of the notes of said composition.

Specifically the marshmallow accord had increased vanilla components by increasing the overall wt % of the key contributors of that accord.

In the raspberry accord the perfumer included an additional key contributor whilst reducing the wt % of the raspberry keytone which has a low ODT.

In the rose accord the perfumer substituted one of the key contributors whilst also reducing the wt % of the phenyl ethyl alcohol.

As with the previous Examples, the fragrance was allowed to emanate within a sensory booth before a panel of experienced sensory panels were exposed as part of a blind, balanced, randomised and sequential monadic testing protocol thereto. The panel comprised a minimum of 20 panelists, both male and female. Example 3 was presented alongside conceptually matched distinctive olfactive concepts designating rose, marshmallow and berry and every time a panellist was exposed to the booth they were asked to record which olfactive concept they smelt. When they declared that they smelt a different olfactive concept to the olfactive concept they had declared previously this was (unbeknown to the panellist) recorded as a "switch".

There was a theoretical distribution of 100% switches and 0% non-switches at the conclusion of the testing but the expected/practical distribution to be indicative of a fragrance presenting more than one distinctive fragrance accord was 70% switches and 30% non-switches. The recorded results were subjected to a chi-squared test.

The obtained results showed that Example 3 is significantly validated as a multi-fragrance accord fragrance @95% confidence level.

The invention claimed is:

1. A fragrance composition comprising: at least two different fragrance accords wherein at least 30 wt % of each fragrance accord comprises a key contributor(s) of said fragrance accord, wherein the key contributor(s) have an odour detection threshold, and wherein the average of the odour detection thresholds of said key contributor(s) for each fragrance accord is within the same order of magnitude as the average of the odour detection thresholds of the key contributor(s) for said other fragrance accord(s).

2. The composition according to claim 1, wherein the fragrance composition is provided with at least three fragrance accords.

3. The composition according to claim 1, wherein the fragrance composition is provided with between two to five fragrance accords.

4. The composition according to claim 1, wherein the fragrance composition is provided with three fragrance accords.

5. The composition according to claim 1, wherein the base note(s) of the fragrance accords comprise less than 15 wt % of the notes of said accord.

6. The composition according to claim 1, wherein the base note(s) of the fragrance accords comprise less than 12.5 wt % of the notes of said accord.

7. The composition according to claim 1, wherein the base note(s) of the fragrance accords comprise less than 10 wt % of the notes of said accord.

8. The composition according to claim 1, wherein the base note(s) of the fragrance accords comprise substantially 7.5 wt %+/−1.5 wt % of the notes of said accord.

9. The composition according to claim 1, wherein the middle note(s) of the fragrance accords comprise greater than 30 wt % of the notes of said accord and the top note(s) of the fragrance accords comprise greater than 30 wt % of the notes of said accord, wherein the % of notes of the overall accord equals 100 wt %.

10. The composition according to claim 1, wherein the middle note(s) of the fragrance accords comprise greater than 40 wt % of the notes of said accord and the top note(s) of the fragrance accords comprise greater than 40 wt % of the notes of said accord, wherein the % of notes of the overall accord equals 100 wt %.

11. The composition according to claim 1, wherein an odour slope of each fragrance accord expressed graphically with intensity on the y-axis (1-10) and concentration on the x-axis (µg/L) in the fragrance composition has a similar gradient wherein a similar gradient is understood to mean gradients within 50 wt % of each other.

12. The composition according to claim 1, wherein each fragrance accord in the fragrance composition of the present invention may comprise of between 5-49.9% wt of the composition.

13. The composition according to claim 1, wherein the fragrance compositions of the present invention may comprise between 1-90% wt of technical accords.

14. The composition according to claim 1, wherein the fragrance composition comprises between 0-10% wt of MOC accords.

15. The composition according to claim 1, wherein a backbone is provided in the composition, wherein said backbone comprises at least one of: odiferous materials; bulk carriers and/or solvents.

16. A method of making a fragrance composition having at least two different fragrance accords comprising the steps of: matching said at least two different fragrance accords by providing that at least 30% wt of a key contributor(s) of each fragrance accord has an average odour detection threshold within the same order of magnitude as the average of the odour detection thresholds of the key contributor(s) of each other fragrance accord.

17. The method according to claim 16, wherein the fragrance composition is provided with at least three fragrance accords.

18. The method according to claim 16, wherein the fragrance composition is provided with between two to five fragrance accords.

19. The method according to claim 16, wherein the fragrance composition is provided with three fragrance accords.

20. The method according to claim 16, wherein the base note(s) of the fragrance accords comprise less than 15 wt % of the notes of said accord.

21. The method according to claim 16, wherein the base note(s) of the fragrance accords comprise less than 12.5 wt % of the notes of said accord.

22. The method according to claim 16, wherein the base note(s) of the fragrance accords comprise less than 10 wt % of the notes of said accord.

23. The method according to claim 16, wherein the base note(s) of the fragrance accords comprise substantially 7.5 wt %+/−1.5 wt % of the notes of said accord.

24. The method according to claim 16, wherein the middle note(s) of the fragrance accords comprise greater than 30 wt % of the notes of said accord and the top note(s) of the fragrance accords comprise greater than 30 wt % of the notes of said accord, wherein the % of notes of the overall accord equals 100 wt %.

25. The method according to claim 16, wherein the middle note(s) of the fragrance accords comprise greater than 40 wt % of the notes of said accord and the top note(s) of the fragrance accords comprise greater than 40 wt % of the notes of said accord, wherein the % of notes of the overall accord equals 100 wt %.

26. The method according to claim 16, wherein an odour slope of each fragrance accord expressed graphically with intensity on the y-axis (1-10) and concentration on the x-axis (μg/L) in the fragrance composition has a similar gradient wherein a similar gradient is understood to mean gradients within 50 wt % of each other.

27. The method according to claim 16, wherein each fragrance accord in the fragrance composition of the present invention may comprise of between 5-49.9% wt of the composition.

28. The method according to claim 16, wherein the fragrance compositions of the present invention may comprise between 1-90% wt of technical accords.

29. The method according to claim 16, wherein the fragrance composition comprises between 0-10% wt of MOC accords.

30. The method according to claim 16, wherein a backbone is provided in the composition, wherein said backbone comprises at least one of: odiferous materials; bulk carriers and/or solvents.

31. A method of attenuating fragrance habituation comprising the steps of emanating a fragrance composition comprising at least two different fragrance accords and wherein said fragrance composition comprises: at least two different fragrance accords wherein at least 30 wt % of each fragrance accord comprises a key contributor(s) of said fragrance accord, wherein the key contributor(s) have an odour detection threshold, and wherein the average of the odour detection thresholds of said key contributor(s) for each fragrance accord is within the same order of magnitude as the average of the odour detection thresholds of the key contributor(s) for said other fragrance accord(s).

32. The method according to claim 31, wherein the fragrance composition is provided with at least three fragrance accords.

33. The method according to claim 31, wherein the fragrance composition is provided with between two to five fragrance accords.

34. The method according to claim 31, wherein the fragrance composition is provided with three fragrance accords.

35. The method according to claim 31, wherein the base note(s) of the fragrance accords comprise less than 15 wt% of the notes of said accord.

36. The method according to claim 31, wherein the base note(s) of the fragrance accords comprise less than 12.5 wt % of the notes of said accord.

37. The method according to claim 31, wherein the base note(s) of the fragrance accords comprise less than 10 wt % of the notes of said accord.

38. The method according to claim 31, wherein the base note(s) of the fragrance accords comprise substantially 7.5 wt %+/−1.5 wt % of the notes of said accord.

39. The method according to claim 31, wherein the middle note(s) of the fragrance accords comprise greater than 30 wt % of the notes of said accord and the top note(s) of the fragrance accords comprise greater than 30 wt % of the notes of said accord, wherein the % of notes of the overall accord equals 100 wt %.

40. The method according to claim 31, wherein the middle note(s) of the fragrance accords comprise greater than 40 wt % of the notes of said accord and the top note(s) of the fragrance accords comprise greater than 40 wt % of the notes of said accord, wherein the % of notes of the overall accord equals 100 wt %.

41. The method according to claim 31, wherein an odour slope of each fragrance accord expressed graphically with intensity on the y-axis (1-10) and concentration on the x-axis (μg/L) in the fragrance composition has a similar gradient wherein a similar gradient is understood to mean gradients within 50 wt % of each other.

42. The method according to claim 31, wherein each fragrance accord in the fragrance composition of the present invention may comprise of between 5-49.9% wt of the composition.

43. The method according to claim 31, wherein the fragrance compositions of the present invention may comprise between 1-90% wt of technical accords.

44. The method according to claim 31, wherein the fragrance composition comprises between 0-10% wt of MOC accords.

45. The method according to claim 31, wherein a backbone is provided in the composition, wherein said backbone comprises at least one of: odiferous materials; bulk carriers and/or solvents.

46. A multi-fragrance accord fragrance composition comprising: three different fragrance accords at least 30 wt % of each fragrance accord comprises a key contributor(s) of said fragrance accord, wherein the key contributor(s) have an odour detection threshold, and wherein the average of the odour detection thresholds of said key contributor(s) for each fragrance accord is within the same order of magnitude as the average of the odour detection thresholds of the key contributor(s) for said other fragrance accord(s).

47. The composition according to claim 46, wherein the base note(s) of the fragrance accords comprise less than 15 wt % of the notes of said accord.

48. The composition according to claim 46, wherein the base note(s) of the fragrance accords comprise less than 12.5 wt % of the notes of said accord.

49. The composition according to claim 46, wherein the base note(s) of the fragrance accords comprise less than 10 wt % of the notes of said accord.

50. The composition according to claim 46, wherein the base note(s) of the fragrance accords comprise substantially 7.5 wt %+/−1.5 wt % of the notes of said accord.

51. The composition according to claim 46, wherein middle note(s) of the fragrance accords comprise greater than 30 wt % of the notes of said accord and the top note(s) of the fragrance accords comprise greater than 30 wt % of the notes of said accord, wherein the % of notes of the overall accord equals 100 wt %.

52. The composition according to claim 46, wherein the middle note(s) of the fragrance accords comprise greater than 40 wt % of the notes of said accord and the top note(s) of the fragrance accords comprise greater than 40 wt % of the notes of said accord, wherein the % of notes of the overall accord equals 100wt %.

53. The composition according to claim 46, wherein an odour slope of each fragrance accord expressed graphically with intensity on the y-axis (1-10) and concentration on the x-axis (μg/L) in the fragrance composition has a similar gradient wherein a similar gradient is understood to mean gradients within 50 wt % of each other.

54. The composition according to claim 46, wherein each fragrance accord in the fragrance composition of the present invention may comprise of between 5-49.9% wt of the composition.

55. The composition according to claim 46, wherein the fragrance compositions of the present invention may comprise between 1-90% wt of technical accords.

56. The composition according to claim 46, wherein the fragrance composition comprises between 0-10% wt of MOC accords.

57. (The composition according to claim 46, wherein a backbone is provided in the composition, wherein said backbone comprises at least one of: odiferous materials; bulk carriers and/or solvents.

* * * * *